United States Patent [19]

Letoffe et al.

[11] Patent Number: 4,956,436

[45] Date of Patent: * Sep. 11, 1990

[54] TIN MONOCHELATE CATALYSIS OF ORGANOPOLYSILOXANE COMPOSITIONS

[75] Inventors: Michel Letoffe, Sainte Foy Les Lyon; Claude Millet, Saint-Priest; Serge Serafini, Venissieux, all of France

[73] Assignee: Rhone-Poulenc Chimie, Courbevoie, France

[*] Notice: The portion of the term of this patent subsequent to Oct. 10, 2006 has been disclaimed.

[21] Appl. No.: 211,916

[22] Filed: Jun. 27, 1988

[30] Foreign Application Priority Data

Jun. 25, 1987 [FR] France ................... 87 09180

[51] Int. Cl.$^5$ ............................................ C08G 77/06
[52] U.S. Cl. ...................... 528/18; 524/860; 524/863; 528/19
[58] Field of Search ............ 528/18, 19; 524/860, 524/863

[56] References Cited

U.S. PATENT DOCUMENTS

| | | | |
|---|---|---|---|
| 4,517,337 | 5/1985 | Lockhart et al. | 524/859 |
| 4,554,310 | 11/1985 | Wengrovius et al. | 524/715 |

FOREIGN PATENT DOCUMENTS 0147323  7/1985  European Pat. Off. .

*Primary Examiner*—Melvyn I. Marquis
*Attorney, Agent, or Firm*—Burns, Doane, Swecker & Mathis

[57] ABSTRACT

Organopolysiloxane compositions curable into elastomeric state, whether in single- or two-component form, comprise an $\alpha,\omega$-dihydroxypolydiorganopolysiloxane oil, a crosslinking agent therefor, optionally, inorganic fillers and an adhesion promoter, and a catalytically effective amount of a pentacoordinated tin monochelate produced by reacting a $\beta$-dicarbonyl compound with an organotin salt.

6 Claims, No Drawings

TIN MONOCHELATE CATALYSIS OF ORGANOPOLYSILOXANE COMPOSITIONS

BACKGROUND OF THE INVENTION

1. Field of the Invention:

The present invention relates to novel curable polyorganosiloxane compositions and, more especially, to such novel polyorganosiloxane compositions containing a catalytically effective amount of a tin crosslinking catalyst produced by reacting a $\beta$-dicarbonyl compound with an organotin salt.

2. Description of the Prior Art:

Many tin compounds have heretofore been proposed to this art as a catalyst for crosslinking polyorganosiloxane compositions and, in particular, RTV compositions (room temperature vulcanizable compositions), whether in a single pack or in two packs, otherwise known as single- or two-component compositions.

The most widely used compounds are tin carboxylates such as tributyltin monooleate, tin 2-ethylhexanoate or dialkyltin dicarboxylates such as dibutyltin dilaurate and dibutyltin diacetate (see Noll, *Chemistry and Technology of Silicones*, page 337, Academic Press, 1968—2nd edition).

In U.S. Pat. No. 3,186,963, such a tin catalyst is described which is the reaction product of a dialkyldialkoxysilane with a tin carboxylate.

In Belgian Pat. No. 842,305, the catalyst is the reaction product of an alkyl silicate or of an alkyltrialkoxysilane with dibutyltin diacetate.

And in U.S. Pat. No. 3,708,467, a catalyst system is described which is a mixture of certain tin salts with a specific titanium chelate, in a single-component composition.

Lastly, in U.S. Pat. Nos. 4,517,337 and 4,554,310 the use of diorganotin bis($\beta$-diketone) is described for the crosslinking of neutral single-component compositions (U.S. Pat. Nos. 4,517,337 and 4,554,310) or for single- and two-component compositions (EP-A-147,323).

Although EP-A-147,323 represents a significant advance in the quest for a tin catalyst useful for both single- and two-component compositions, it has become apparent that diorganotin bis($\beta$-diketonates) exhibit a core setting time which is a little too slow, particularly in the case of the two-component compositions.

The problem which typically arises in the case of the single-component compositions is essentially that of storage stability and of the retention of physicochemical properties (extrudability, pourability, setting time) of the composition and maintaining these properties by the reticulate (mechanical properties, hardness, elongation, tear strength, adhesiveness, and the like).

Thus, need exists in this art for a catalyst which crosslinks very rapidly on exposure to atmospheric moisture, not only on the surface thereof, but which at the same time provides a thorough crosslinking uniformly therethrough which is as complete as possible, and which is also active in minor amounts, while reducing to the minimum the reticulate degradation reactions which are inherent in the presence of tin.

With regard to the three-dimensional shaped article or reticulate thus obtained, the same problems as exist in the case of the single-component compositions also exist in the case of the two-component compositions, but, in addition, the exposure or open time (that is to say, the time during which the composition may be employed after mixing without hardening) must be sufficiently long to permit its effective use, but sufficiently short to produce a molded object capable of being handled not later than 24 hours after the production thereof.

This catalyst must therefore provide a good compromise between the open time of the catalyzed mixture and the time after which the molded object can be handled In addition, the catalyst must impart to the catalyzed mixture a spreading time which does not vary as a function of the storage period.

SUMMARY OF THE INVENTION

Accordingly, a major object of the present invention is the provision of an improved catalyst system adapted for the crosslinking of both the single- and two-component elastomer compositions.

Another object of the present invention is the provision of an improved catalyst system which simultaneously meets the storage, use and crosslinking constraints common to both types of elastomer compositions, while addressing the specific problems presented by each, without, however, initiating detrimental secondary effects in either case.

Briefly, the present invention features improved organopolysiloxane compositions comprising, on the one hand, a silicone base polymer capable of being cured into an elastomer by a polycondensation reacting beginning at ambient temperature and, on the other hand, a catalytically effective amount of the product of reaction between (a) a tin salt of the formula:

$$(X)_2 SnR_1 R_2 \qquad (1)$$

in which the symbols $R_1$ and $R_2$, which may be identical or different, are each an optionally substituted, monovalent $C_1$–$C_{18}$ hydrocarbon radical and the symbol X is a halogen (chlorine, bromine, iodine, fluorine) atom or a monocarboxylate radical of the formula $R_6COO$ in which the symbol $R_6$ has the same definition, as the symbol $R_1$ above, and preferably denotes a linear or branched chain $C_1$–$C_{18}$ alkyl radical, with (b) a $\beta$-dicarbonyl compound of the formula:

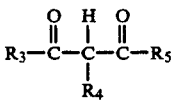

$$R_3 - \overset{\overset{\displaystyle O}{\|}}{C} - \overset{\overset{\displaystyle H}{|}}{\underset{\underset{\displaystyle R_4}{|}}{C}} - \overset{\overset{\displaystyle O}{\|}}{C} - R_5 \qquad (2)$$

or, more simply, having the abbreviated formula CH, in which:

the symbols $R_3$ and $R_5$, which may be identical or different, are each a radical $R_1$ or $R_2$, a hydrogen atom, a $C_1$–$C_5$ alkoxy radical or an $Si(R_1)_3$ silyl radical;

the symbol $R_4$ is a hydrogen atom, or an optionally halogenated $C_1$–$C_8$ hydrocarbon radical, with the proviso that R4 and R5 may together form, with the carbon atoms from which they depend, a divalent $C_5$–$C_{12}$ cyclic hydrocarbon radical, or an optionally substituted such cyclic radical bearing at least one chloro, nitro and/or cyano substituent.

DETAILED DESCRIPTION OF THE PREFERRED EMBODIMENTS OF THE INVENTION

More particularly according to the present invention, the preferred organic derivatives of the formula (1) are di-n-butyltin dilaurate, di-n-octyltin dilaurate, di-n-butyltin diacetate, di-n-butyltin di-2-ethylhexanoate, di-n-octyltin di-2-ethylhexanoate, di-n-butyltin diversatate and di-n-octyltin diversatate.

Exemplary of such compounds of the formula (1), useful for the synthesis of products of the formula (3) below, representative are:
$(CH_3COO)_2Sn(CH_3)_2$,
$(CH_3COO)_2Sn(n.C_4H_9)_2$,
$CH_3(CH_2)_8COO_2Sn(CH_3)_2$,
$CH_3(CH_2)_3CH(C_2H_5)COO_2Sn(CH_3)_2$,
$(CH_3COO)_2Sn(CH_2C_6H_5)_2$,
$CH_3(CH_2)_3CH(C_2H_5)COO_2Sn(n.C_4H_9)_2$,
$CH_3(CH_2)_{14}COO_2Sn(n.C_4H_9)_2$,
$CH_3(CH_2)_3CH(C_2H_5)COO_2Sn(n.C_8H_{17})_2$,
$CH_3(CH_2)_7CH=CH(CH_2)_7COO_2Sn(n.C_4H_9)_2$,
$CH_3(CH_2)_{12}COO_2Sn(C_2H_5)_2$,
$CH_3(CH_2)_{10}COOSn(n.C_4H_9)_2$,
$CH_3(CH_2)_{10}COO_2Sn(n.C_8H17)_2$.

Also representative are the dialkyltin versatates described in British Pat. No. 1,289,900.
$(C_2H_5)_2SnF_2$,
$(tertio-C_4H_9)_2SnCl_2$,
$(iso-C_3H_7)_2SnBr_2$,
$(CH_2=CH)_2SnCl_2$,
$(CH_3CCl=CH-CH_2)_2SnCl_2$,
$(C_4H_9)(C_6H_5)SnCl_2$,
$C_6H_5(CH_2=CH)SnCl_2$.

The preparation of these organic tin derivatives is known to this art; compare, in particular, the text mentioned above, *The Chemistry of Organotin Compounds* by R. C. Poller, published in 1970 by Academic Press; the three-volume text, *Organotin Compounds*, edited by Albert K. Sawyer and published in 1972 by Marcel Dekker; and the collective text edited by A. Seyferth and R. B. King, published by the Elsevier Scientific Publishing Company, a collection entitled "Organometallic Chemistry Reviews, Annual Surveys: Silicon-Germanium -Tin-Lead".

Exemplary of the β-dicarbonyl compounds, including the β-diketones and β-ketoesters of formula (2), are 2,4-heptanedione, 2,4-decanedione, 2-methyl-2-decene-6,8-dione, 2-methyl-2-nonene-6,8-dione, 1-stearoyl-2-octanone, triacetylmethane, ethyl 7,9-dioxodecanoate, benzoylacetone, 1-benzoyl-2-octanone, 1,4-diphenyl-1,3-butanedione, stearoylacetophenone, palmitoylacetophenone, 1-benzoyl-4-methyl-2-pentanone, benzoyloctacosanoylmethane, 1,4-bis(2,4-dioxobutyl)-benzene, para-methoxybenzoylstearoylmethane, 2-allyl-1-phenyl-1,3-butanedione, 2-methyl-2-acetylacetaldehyde, benzoylacetaldehyde, acetoacetyl-3-cyclohexene, bis(2,6-dioxocyclohexyl)methane, 2-acetyl-1-oxo-1,2,3,4-tetrahydronaphthalene, 2-palmitoyl-1-oxo-1,2,3,4-tetrahydronaphthalene, 1-oxo-2-stearoyl-1,2,3,4-tetrahydronaphthalene, 2-acetyl-1-cyclohexanone, 2-benzoyl-1-cyclohexanone, 2-acetyl-1,3-cyclohexanedione, dibenzoylmethane, tribenzoylmethane, bis(-paramethoxybenzoyl)methane, 1-(N-phenylcarbamoyl)-1-benzoylacetone, 1-(N-phenylcarbamoyl)-1-acetylacetone, ethyl acetylacetate, acetylacetone and 1,1,1-trifluoro-3-benzoylacetone.

These various β-diketones of formula (2) are typically prepared by known procedures, such as those described in *Organic Reactions* by R. Adams et al (1954 edition, volume VIII, pages 59 et seq). Certain more specific syntheses are described in *Rec. Trav. Chim. PaysBas*, (1897), volume 16, pages 116 et seq, by M. J. Kramers, in *J. Chem. Soc.*, (1925), volume 127, pages 2891 et seq, by G. T. Morgan et al, or in *J. Chem. Soc.*, (1941), pages 1582 et seq, by R. Robinson and E. Seijo.

It has been demonstrated that the reaction described above results in the formation of a monochelate of pentacoordinated tin of valency IV of the formula:

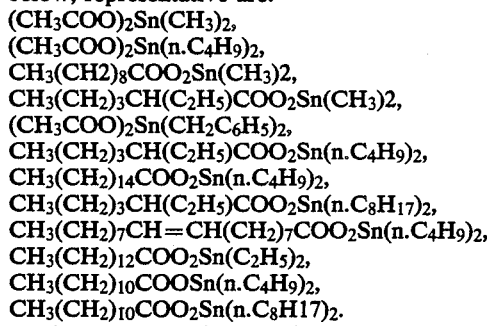

or, more simply, having the abbreviated formula $R_1R_2SnCX$ in which the symbols X, $R_1$, $R_2$, $R_3$, $R_4$ and $R_5$ are as defined above.

The monochelates of formula (3) may be identified by the analytical techniques of NMR spectroscopy ($^{119}$Sn, $^{13}$C and $^1$H nuclear magnetic resonance), by mass spectroscopy and by measurement of the Mossbauer effect.

It has been found, however, that in the present state of the art of analytical techniques, the 119Sn NMR analytical method such as described, in particular, in the article by Peter J. Smith, "Chemical Shifts of 119Sn Nuclei in Organotin Compounds", page 291, et seq, published in the *Annual Reports on NMR Spectroscopy*. volume 8, 1978, Academic Press, is a method which is by itself sufficiently accurate to the characterize the various tin compounds present within a mixture, particularly within a reaction mixture, and to make it possible to determine the chemical formulae of most of these compounds.

The fundamental parameter evaluated by $^{119}$Sn NMR is the value of the chemical shift, expressed in parts per million (ppm) relative to a reference (generally tetramethyltin).

The value of the chemical shift is particularly sensitive to the electronegativity of the groups carried by the tin and to the change in the coordination number of the tin atom. Specific studies of characterization of organostannic derivatives using $^{119}$Sn NMR are described in particular by A. G. Davies and P. J. Smith, *Comprehensive Organo-metallic Chemistry*. 11 Tin, pages 523 to 529 and by J. Otera, *J. of Organomet. Chem..* 221. pages 57-61 (1981).

Analysis of the reaction mixtures obtained according to the process of the present invention has made it possible to demonstrate that the production of the tin monochelate of formula (3) without formation of distannoxane of formula $XR_1R_2SnOSnR_1R_2X$, of tin oxide $R_1R_2SnO$ and of bischelate of hexacoordinated pentavalent tin of formula $R_1R_2SnC_2$ in the case where a molar ratio of the starting materials of (2)/(1) ranging from 1 to 3 is employed. In this case, the equilibrium reaction mixture in practice contains, as tin compound, only the monochelate $R_1R_2SnCH$ and the tin salt of formula (1). In this case, the concentrations in molar %, calculated in gram-atoms of tin metal are, in principle,
$R_1R_2SnCX$: 10 to 50
$R_1R_2SnX_2$: 90 to 50

In the above formulae, the symbols $R_1$ and $R_2$, which may be identical or different, denote optionally substituted, monovalent $C_1-C_{18}$ hydrocarbon radicals More especially, these organic radicals include:
(i) $C_1-C18$ alkyl radicals, halogenated or otherwise, such as methyl, ethyl, propyl, isopropyl, butyl, isobutyl, secondary butyl, tert-butyl, pentyl, hexyl, heptyl, 2-ethylhexyl, octyl, decyl, dodecyl, octadecyl, chloromethyl and 2,5-dichloroethyl radicals;

(ii) $C_2$–$C_{18}$ alkenyl radicals, halogenated or otherwise, such as vinyl, allyl, methallyl, 2-butenyl, 2-pentenyl, 3-octenyl, 5-fluoro-2-pentenyl and pentadecenyl radicals;

(iii) $C_4$–$C_{10}$ cycloalkyl radicals, halogenated or otherwise, such as cyclopentyl, cyclohexyl, methylcyclohexyl, cyclooctyl, 3,4-dichlorocyclohexyl and 2,6-dibromocycloheptyl radicals;

(iv) $C_6$–$C_{15}$ mononuclear aryl radicals, halogenated or otherwise, such as phenyl, tolyl, xylyl, cumenyl, chlorophenyl, dichlorophenyl, trichlorophenyl, difluorophenyl and trifluoromethylphenyl radicals, (v) $C_7$–$C_{15}$ mononuclear arylalkyl radicals, halogenated or otherwise, such as phenylmethyl, phenylethyl, phenylpropyl and trifluoromethylphenylethyl radicals.

The symbols $R_3$ and $R_5$, which may be identical or different, have the same definitions as $R_1$ and $R_2$, namely, optionally substituted, monovalent $C_1$–$C_{18}$ hydrocarbon radicals, and may additionally denote hydrogen atoms, cyanoalkyl radicals containing a $C_2$–$C_4$ alkyl moiety, $C_1$–$C_5$ alkoxy radicals or $-Si(R_1)_3$ silyl radicals.

Cyanoehyl, cyanopropyl and cyanobutyl radicals are exemplary of the cyanoalkyl radicals, and ethoxy and propoxy radicals are exemplary of the alkoxy radicals The symbol $R_4$ denotes the hydrogen atom, or an optionally halogenated $C_1$–$C_8$ hydrocarbon radical.

More especially, this radical includes alkyl radicals, halogenated or otherwise, such as methyl, ethyl, propyl, butyl, hexyl and octyl radicals and mononuclear aryl radicals, halogenated or otherwise, such as phenyl, tolyl, chlorophenyl and dichlorophenyl radicals.

In addition, on coupling with $R_5$, $R_4$ forms with $R_5$ a divalent $C_5$–$C_{12}$ cyclic hydrocarbon radical, substituted or otherwise by chloro, nitro or cyano radicals.

Representative such ring members are those of the formulae:

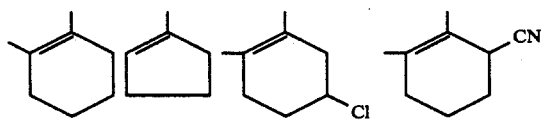

The symbol X is a halogen (chlorine, bromine, iodine, fluorine) atom or a monocarboxylate radical of the formula $R_6COO$ in which the symbol $R_6$ has the same definition as the symbol $R_1$ above, and preferably denotes a linear or branched chain $C_1$–$C_{18}$ alkyl radical.

Unless otherwise indicated, all percentages and parts given herein by weight.

The monochelate of formula (3) or the equilibrium reaction mixture, referred to hereinafter as the tin catayIst according to the invention, is stable in storage in a closed container, at ambient temperature.

It is used to permit or facilitate the curing of the organopolysiloxane base to a silicone elastomer, beginning at ambient temperature.

These bases, which cure (crosslink) by polycondensation reactions, are well known to this art. After having been catalyzed, in most cases by means of a metallic derivative of a carboxylic acid, they are utilized for the manufacture of seals, of water-repellent coatings, of molds, of coating materials, for the adhesive bonding and the assembly of the widest variety of materials, for coating organic and inorganic fibers, and the like.

These bases are described in detail, in particular, in many patents and they are available commercially.

These silicone bases may be single-component, that is to say, packaged in a single pack this is stable in storage in the absence of moisture and capable of being cured in the presence of moisture, in particular of moisture contributed by the surrounding air or by the water generated within the base when it is used.

These single-component bases are generally of three types, as described in further detail below, and are catalyzed by the incorporation of a catalytically effective amount of the monochelate of formula (3) or of the equilibrium mixture containing the monochelate of formula (3). This catalytically effective amount is on the order of 0.0001 to 5 parts, preferably from 0.01 to 3 parts per 100 parts of the single-component base Other than the single-component bases, it is also possible to employ two-component bases, that is to say, those packaged in two packs, which cure as soon as the tin catalyst is incorporated. They are packaged in two separate fractions, it being possible for one of the fractions, for example, to contain only the tin catalyst or the mixture of the catalyst with the crosslinking agent.

The catalytically effective amount of tin catalyst is on the order of 0.01 to 10 parts, preferably from 0.1 to 5 parts per 100 parts of the two-component base.

As already indicated above, single-component and two-component silicone bases which cure (crosslink) via polycondensation reactions are described in detail in the literature and are available commercially.

These bases are generally prepared from the following constituents:

(A) 100 parts of an $\alpha,\omega$-dihydroxypolydiorganosiloxane polymer, having a viscosity of 500 to 1,000,000 mPa.s at 25° C., comprising recurring units of the formula $(R_2)SiO$ where the symbols R, which may be identical or different, are hydrocarbon radicals containing from 1 to 10 carbon atoms, optionally substituted by halogen atoms or cyano groups;

(B) 0.5 to 20 parts of a crosslinking agent selected from among organosilicon compounds containing more than two hydrolyzable groups bonded to silicon atoms, per molecule;

(C) 0 to 250 parts of inorganic fillers; and (D) 0 to 20 parts of an adhesion promoter.

The radical R is typically methyl, ethyl, propyl, phenyl, vinyl or a 3,3,3-trifluoropropyl radical, at least 80% of the groups R being methyl.

A first type of single-component formula results from mixing the polymer A with a crosslinking agent B, which advantageously is a silane of the formula:

$$R_aSi(Z)_{4-a} \qquad (4)$$

in which R is as defined above for the polymer A, and Z is a hydrolyzable group advantageously selected from among N-substituted amino, N-substituted amido, N,N-disubstituted aminoxy, ketimonoxy, aldiminoxy, alkoxy, alkoxyalkylenoxy, enoxy and acyloxy groups, and a denotes 0 or 1.

Single-component bases of this type are described in detail, particularly in European patent applications EP-A-141,685 and EP-A-147,323, hereby incorporated by reference.

The most widely used compositions are those in which Z is an acyloxy and ketiminoxy group, which are described in greater detail in European patent application EP-A-102,268, also hereby incorporated by reference.

Two-component flowing compositions, in which Z is an acyloxy group, and whose crosslinking is accelerated by the addition of an alkaline earth metal hydroxide or phosphate are described in European patent applications EP-A-118,325 and EP-A-117,772, also hereby incorporated by reference.

In a second type of single-component base, the starting point is not a mixture of A and B, but the product $A_1$ of reaction of A with B. In general, the hydrolyzable group is an alkoxy group and the composition additionally contains from 0 to 15 parts of crosslinking agent B per 100 parts of functionalized polymer $A_1$.

The reaction of A with B can be carried out in the presence of various catalysts such as an organic amine (U.S. Pat. No. 3,542,901), an organic titanium derivative (U. S. Pat. No. 4,111,890), a carbamate (European patent application EP-A-210,402) and an N,N-disubstituted hydroxylamine (European patent application EP-A-70,786).

To these single-component bases there may be added adhesion promoters (D), selected from among organosilicon compounds simultaneously bearing, on the one hand organic groups substituted by radicals selected from among amino, ureido, isocyanate, epoxy, alkenyl, isocyanurate, hydantoyl, guanidino and mercaptoester radicals and, on the other hand, hydrolyzable groups, generally alkoxy groups bonded to the silicon atoms. Examples of such adhesion promoters are described in U.S. Pat. Nos. 3,517,001, 4,115,356, 4,180,642, 4,273,698 and 4,356,116, and in European patent applications EP-A-31,996 and EP-A-74,001.

A third type of single-component bases are those prepared by mixing 100 parts of polymer A, from 0.5 to 20 parts of crosslinking agent B which is a polyalkoxysilane (formula 4), Z =alkoxy or alkoxyalkylenoxy, from 0 to 250 parts of inorganic fillers and from 0.5 to 15 parts of a compound $D_1$ selected from among:

(i) $D_{1-a}$: a primary organic amine having a pKb of less than 5 in aqueous medium, an aminoorganosilane and an aminoorganopolysiloxane bearing at least one $C_1-C_{15}$ organic group linked by a Si—C bond to the silicon atom per molecule, and substituted by at least one amino radical and at least one $C_1-C_5$ alkoxy or $C_3-C_6$ alkoxyalkyleneoxy radical; and (ii) $D_{1-b}$: an organic titanium or zirconium derivative bearing an organoxy and/or β-diketonato group.

Single-component bases comprising $D_{1-a}$ are described in European patent application EP-A-21,859 and those comprising $D_{1-b}$ are described in French Patents FR-A-2,121,289 and FR-A-2,121,631, also hereby incorporated by reference.

The two-component bases are formed by mixing:
(a) 100 parts of polymer (A)
(b) 1 to 20 parts of a crosslinking agent selected from among a silane of formula (4) above, and the products of partial hydrolysis of the silane of formula (4);
(c) 0 to 150 parts of inorganic fillers; and
(d) 0 to 20 parts of an adhesion promoter.

These compositions are well known to this art; in particular, they are described in European patent applications EP-A-10,478, EP-A-50,358 and EP-A-184,966 and in U.S. Pat. Nos. 3,801,572 and 3,888,815.

The adhesion promoter employed may be the silanes D employed in the case of the single-component bases and silanes bearing a morpholino group (EP-A-184,966) or an organic radical comprising a tertiary nitrogen atom (U. S. Pat. Nos. 3,801,572 and 3,888,815).

The products of partial hydrolysis of the alkoxysilanes of formula (4), which are usually referred to as alkyl polysilicates, are well-known products which exhibit the property of dissolving in the usual hydrocarbon solvents such as toluene, xylene, cyclohexane and methylcyclohexane; the most widely used material is ethyl polysilicate 40 ® with a silica content of 40%, a value obtained after total hydrolysis of the ethoxy radicals.

The inorganic fillers (c) employed in the case of the single- and two-component bases are very finely divided materials whose mean particle diameter is below 0.1 micrometer. These fillers include the pyrogenic silicas and precipitated silicas; their BET specific surface area is generally greater than 40 m$^2$/g.

These fillers may also be in the form of more coarsely divided materials, with a mean particle diameter greater than 0.1 micrometer. Examples of such fillers which are representative are ground quartz, diatomaceous silicas, calcium carbonate, calcined clay, rutile-type titanium dioxide, iron, zinc, chromium, zirconium and magnesium oxides, the various forms of alumina (hydrated or otherwise), boron nitride, lithopone, barium metaborate, barium sulfate and ballotini; their specific surface area is generally below 30 m$^2$/g.

These fillers may have been surface-modified by treatment with the various organosilicon compounds usually employed for this purpose. Thus, these organosilicon compounds may be organochlorosilanes, diorganocyclopolysiloxanes, hexaorganodisiloxanes, hexaorganodisilazanes or diorganocyclopolysilazanes (French Pat. Nos. FR-A-1,126,884, FR-A-1,136,885, FR-A-1,236,505 and British Pat. No. GB-A-1,024,234). In most cases, the treated fillers contain from 3 to 30% of their weight of organosilicon compounds.

The fillers may be a mixture of a number of types of fillers of different particle size distribution; thus, for example, they may comprise 30 to 70% of finely divided silicas with a BET specific surface area greater than 40 m$^2$/g and of 70 to 30% of more coarsely divided silicas with a specific surface area below 30 m$^2$/g.

The tin catalyst according to the invention is more particularly effective in the case of the single- and two-component silicone bases where the crosslinking agent (B) of formula (4) contains radicals Z which are identical or different, selected from among alkoxy and alkoxyalkylenoxy radicals of formulae $R_7O$ and $R_7OTO$ in which $R_7$ is a $C_1-C_4$ alkyl radical and T denotes a $C_2-C_4$ alkylene group.

In addition, in the case where the silicone base has two components it is possible to use the product of partial hydrolysis of the crosslinking agent (B).

In addition to the fundamental constituents of the single-component and two-component bases, that is to say, (1) the diorganopolysiloxane polymers (A) and/or ($A_1$) blocked by a hydroxyl radical and/or alkoxy radicals at the end of a chain, (2) the organosilicon crosslinking agents (B) bearing hydrolyzable groups, (3) the inorganic fillers and (4) the adhesion promoters (D), other ingredients may be introduced.

These ingredients include organosilicon compounds, chiefly polymers, which are capable of affecting the physical characteristics of the compositions according to the invention (formed by mixing the bases with the tin catalyst) and/or the mechanical properties of the silicone elastomers using these compositions.

These compounds are well known; for example, they include:

(i) $\alpha,\omega$-bis(triorganosiloxy)diorganopolysiloxane polymers having a viscosity of at least 10 mPa.s at 25° C. in which the organic radicals bonded to the silicon atoms are methyl, vinyl and phenyl radicals, preferably at least 80% of the radicals are methyl radicals and not more than 3% are vinyl radicals; $\alpha,\omega$-bis(trimethylsiloxy)-dimethylpolysiloxane oils having a viscosity of 10 mPa.s at 25° C. to 1,500 mPa.s at 15° C. are preferably employed;

(ii) liquid, branched methylpolysiloxane polymers containing from 0.1 to 8% of hydroxyl groups bonded to the silicon atoms, comprising $(CH_3)_3SiO_{0.5}$, $(CH_3)_2SiO$ and $CH_3SiO_{1.5}$ recurring units distributed such as to provide a $(CH_3)_3SiO_{0.5}/(CH_3)_2SiO$ ratio of 0.01 to 0.15 and a $CH_3SiO_{1.5}/(CH_3)_2SiO$ ratio of 0.1 to 1.5;

(iii) $\alpha,\omega$-di(hydroxy)dimethylpolysiloxane oils having a viscosity of 10 to 300mPa.s at 25° C., and $\alpha,\omega$-di(hydroxy)methylphenylpolysiloxane oils having a viscosity of 200 to 5,000 mPa.s at 25° C.; and (iv) diphenylsilanediol and 1,1,3,3-tetramethyldisiloxanediol.

The above $\alpha,\omega$-bis(triorganosiloxy)diorganopolysiloxane polymers may be completely or partly replaced by organic compounds which are inert towards the various constituents of the bases and which are miscible at least with the diorganopolysiloxane polymers (A) or (A$_1$). Specific examples of such organic compounds are mineral oils, petroleum cuts and polyalkylbenzenes obtained by the alkylation of benzene with long-chain olefins, particularly olefins containing 12 carbon atoms obtained by propylene polymerization. Organic compounds of this type appear, for example, in French Pat. Nos. FR-A-2,392,476 and FR-A-2,446,849.

Each of the above organosilicon compounds may be employed in a proportion of 1 to 15o parts, preferably 3 to 75 parts, per 100 parts of diorqanopolysiloxanes (A) or (A$_1$).

Non-organosilicon ingredients may also be introduced, for example heat stabilizers. These compounds improve the heat resistance of the silicone elastomers. They may be carboxylic acid salts, rare earth oxides and hydroxides and more especially ceric oxides and hydroxide, as well as from combustion titanium dioxide and various iron oxides. From 0.1 to 15 parts, preferably from 015 to 12 parts, of heat stabilizers are advantageously employed per 100 parts of the diorganopolysiloxanes (A) or (A$_1$).

In the case of the single-component compositions, to produce the compositions according to the invention it is necessary to employ apparatus which enables the various fundamental constituents, to which the above-mentioned adjuvants and additives are added if desired, to be intimately mixed in the absence of moisture, with and without application of heat.

All these ingredients may be charged into the apparatus in any order of addition. Thus, the diorganopolysiloxane polymers (A) or (A$_1$) and the fillers (C) can first be mixed, and the crosslinkers (B), the compounds (D) and the tin catalyst can then be added to the resulting paste.

It is also possible to mix the polymers (A) or (A$_1$), the crosslinkers (B) and the compounds (D) and subsequently to add the fillers (C) and the tin catalyst. The mixtures may be heated during these operations to a temperature in the range 50–180° C. at atmospheric pressure or at a reduced pressure in order to promote the elimination of volatile materials such as water and polymers of low molecular weight.

The compositions prepared in this manner may be employed as such or in the form of a dispersion in organic diluents. These diluents are preferably conventional commercial products selected from among:

(i) aliphatic, cycloaliphatic or aromatic hydrocarbons, halogenated or otherwise, such as n-heptane, n-octane, cyclohexane, methylcyclohexane, toluene, xylene, mesitylene, cumene, tetralin, decalin, perchloroethylene, trichloroethane, tetrachloroethane, chlorobenzene and orthodichlorobenzene;

(ii) aliphatic and cycloaliphatic ketones such as methyl ethyl ketone, methyl isobutyl ketone, cyclohexanone and isophorone; and (iii) esters such as ethyl acetate, butyl acetate and ethylglycol acetate.

The quantities of diluents introduced must be sufficient to produce stable dispersions which spread easily on the substrates. These quantities depend essentially on the nature and on the viscosity of the initial organopolysiloxane compositions. They may consequently vary within wide proportions; nevertheless, production of dispersions containing from 15 to 85% by weight of diluents is recommended.

The single-component compositions according to the invention, which are used as such, that is to say, undiluted, or in the form of dispersions in diluents, are stable in storage in the absence of water and cure beginning at ambient temperature (after removal of the solvents in the case of dispersions) to form elastomers, in the presence of water.

After the composition as such have been deposited onto solid substrates, in a moist atmosphere, it is found that a process of curing to elastomers takes place, proceeding from the outside towards the inside of the deposited mass. A surface skin forms first and then the crosslinking continues into the depth of the mass.

The complete formation of the skin, which manifests itself as a nonsticky surface feel, requires a period of time which can be in the range from 1 minute to 55 minutes; this time period depends on the relative humidity of the atmosphere surrounding the compositions and on the ease of crosslinking of the latter.

Furthermore, the cure throughout the deposited layers, which must be sufficient to allow the elastomers formed to be demolded and handled, requires a longer period of time. This period depends, in fact, not only on the factors mentioned above in the case of the formation of a nonsticky feel, but also on the thickness of the deposited layers, which thickness generally ranges from 0.5 mm to several centimeters. This longer period of time may range from 10 minutes to 20 hours.

The single-component compositions may be employed for many applications, such as sealing in the building industry, the assembly of a very wide variety of materials (metals, plastics, natural and synthetic rubbers, wood, cardboard, earthenware, brick, ceramic, glass, stone, concrete, masonry components), the insulation of electrical conductors, coating of electronic circuits, and the production of molds used for the manufacture of shaped articles made of synthetic resins or foams.

The above-mentioned dispersions of these compositions in the diluents can be employed for thin-layer impregnation of inorganic, synthetic, organic, metallic, woven or nonwoven products and articles, and for coating metal, plastic or cellulosic sheets. The deposition can be produced, for example, by dipping or by spraying; in the latter case, a spray gun is used which permits uniform coatings with a thickness of 5 to 300 μm to be obtained After the dispersions have been sprayed, the diluents evaporate off and the compositions released cure to a rubbery film.

The production of two-component compositions according to the invention is also carried out by mixing the various constituents in suitable apparatus. To obtain homogeneous compositions it is preferable to mix the polymers (A) with the fillers (C) first; the combination may be heated for at least 30 minutes to a temperature above 80° C. such as to complete the wetting of the fillers by the oils. The other constituents, namely, the crosslinking agents (B), the organic tin derivative and, if desired, various additives and adjuvants, and even water, can be added to the mixture obtained, which is preferably heated to a temperature below 80° C., for example on the order of ambient temperature.

Such compositions are not stable in storage and must therefore be used quickly, for example within a time interval of 40 minutes.

The various additives and adjuvants are the same as those introduced into the single-component compositions In particular, the $\alpha,\omega$-bis(triorganosiloxy)diorganopolysiloxane polymers having a viscosity of at least 10 mPa.s at 25° C. in which the organic radicals bonded to the silicon atoms are methyl, vinyl and phenyl radicals, are representative. $\alpha,\omega$-(Trimethylsiloxy)dimethylpolysiloxane oils having a viscosity of preferably 20 mPa.s at 25° C. to 1,000 mPa.s at 25° C. are generally employed in a proportion not exceeding 150 parts per 100 parts of polymer (A).

The introduction of water in a proportion not exceeding 1 part per 100 parts of polymers (A) is recommended to promote the curing of the two-component compositions which are employed in thick layers whose thickness is, for example, greater than 2 cm.

This water addition is unnecessary if the fillers (C) contain enough of it. To facilitate its incorporation, water is preferably added int he form of a dispersion in a paste comprising, for example, the above-mentioned $\alpha,\omega$-bis(triorganosiloxy)diorganopolysiloxane oils and the fillers (C).

For packaging and storage, the two-component compositions cannot therefore contain all the fundamental constituents, namely, the polymers (A), the crosslinker (B), the fillers (C) and the tin catalyst (E). On an industrial scale, they must be formulated in the form of two components, each being stable in storage.

A first, storage-stable component may, for example, comprise the constituents (A), (B) and (C); it is preferably prepared by introducing the crosslinking agents (B) into the homogeneous mixture formed by compounding the polymers (A) with the fillers (C).

The second component then comprise the tin catalyst.

Other ways of presenting the two-component compositions may be selected; for example, a first component containing the polymers (A) and the fillers (C) and a second component containing the crosslinking agents (B) and the tin catalyst.

In many applications it is preferable that each of the two components be sufficiently fluid such as to easily form compositions whose viscosity ranges, for example, from 10,000 to 800,000 mPa.s at 25° C. when mixed.

These compositions, which remain sufficiently fluid for at least 40 minutes, preferably for at least 80 minutes, after the mixing of the two components, can be employed more especially for the manufacture of silicone elastomer molds. They may, however, be employed for other applications such as coating electronic equipment and coating metallic surfaces or textile or cellulosic substances.

The molds which are manufactured are intended to reproduce articles made of cellular or noncellular materials formed from organic polymers. Among such materials, exemplary are polyurethanes, polyesters, polyamides and polyvinyl chloride. The use of these molds for the reproduction of polyurethane articles is, however, recommended, since they withstand quite well attack by constituents of the mixtures used to produce polyurethanes (in particular polyisocyanates).

The introduction of the tin catalyst according to the invention, at least partly comprising the tin monochelate, makes it possible to attain the best conditions of use in the case of the single- and two-component compositions. It makes it possible to subsequently produce elastomers having stable properties upon use thereof and which are independent of the age and of the storage conditions of the compositions.

In order to further illustrate the present invention and the advantage thereof, the following specific examples are given, it being understood that same are intended as illustrative and in nowise limitative.

EXAMPLE 1

1 mole of 1-benzoyl-4-methyl-2-pentanone and 1 mole of di-n-octyltin di-2-ethylhexanoate were introduced under a nitrogen atmosphere into a 1-liter three-necked roundbottomed flask fitted with a central stirrer, a condenser and a thermometer. Stirring was continued at ambient temperature (20° C.) for one hour. The reaction mixture was analyzed using $^{119}$Sn NMR in the absence of atmospheric moisture.

The results are reported in Table 1 below.

EXAMPLES 2 AND 3

The operating procedure of Example 1 was repeated, except that the quantities introduced were changed.

The results are reported in Table 1 below.

EXAMPLE 4

The operating procedure of Example 1 was repeated, except that 1 mole of di-n-butyltin dilaurate was employed.

The results are reported in Table 1 below.

The reaction may be expressed diagrammatically as follows:

$$a\ R_1R_2SnX_2 + b CH \rightleftharpoons R_1R_2SnCX + XH$$

and a and b representing the molar quantities which were introduced.

XH1: 2-ethylhexanoic acid
XH2: lauric acid

The columns PR1, PR2, PR3 and PR4 report the mol % calculated in gram-atoms of tin metal for the products present in the reaction mixture.

PR1: $R_1R_2SnCX$
PR2: $R_1R_2SnX_2$
PR3: $R_1R_2SnC_2$
PR4: $XR_1R_2SnOSnR_1R_2X$

TABLE 1

| Example | R1 and R2 | a | XH | b | PR1 | PR2 | PR3 | PR4 |
|---|---|---|---|---|---|---|---|---|
| 1 | C8H17 | 1 | XH1 | 1 | 22.0 | 78.0 | 0 | 0 |
| 2 | C8H17 | 1 | XH1 | 1.5 | 22.6 | 77.4 | 0 | 0 |
| 3 | C8H17 | 1 | XH1 | 3 | 31.0 | 69.0 | 0 | 0 |
| 4 | C4H9 | 1 | XH2 | 2 | 21.0 | 79.0 | 0 | 0 |

COMPARATIVE EXAMPLE 5 AND EXAMPLES 6 TO 8

A composition P$_1$ was prepared by mixing:

(i) 100 parts of an α,bis(trimethylsiloxy)dimethylpolysiloxane oil having a viscosity of 10,000 mPa.s at 25° C.;

(ii) 70 parts of an α,ω-bis(trimethylsiloxy)dimethylpolysiloxane oil having a viscosity of 800 mPa.s at 25° C.

(iii) 55 parts of a pyrogenic silica having a specific surface area of 300 m$^2$/g, treated with hexamethyldisilazane;

(iv) 50 parts of ground quartz having a mean particle diameter of 5 micrometers; and (v) 10 parts of a paste made up of 90 parts of the above-mentioned α,ω-dihydroxydimethylpolysiloxane oil, having a viscosity of 10,000 mPa.s at 25° C., 5 parts of a pyrogenic silica having a specific surface area of 150 m$^2$/g and 5 parts of water.

The composition P$_1$ was catalyzed with a crosslinking system containing the catalysts (C) forming the subject of Examples 1 to 3 and partially hydrolyzed ethyl silicate, the concentration of tin catalyst (calculated as weight of metallic tin) being maintained constant.

The composition P$_1$ was catalyzed by mixing 100 parts of this composition with two parts of the crosslinking system containing 82.5 parts of partially hydrolyzed ethyl silicate and 17.5 parts of catalyst (C). The amount of β-diketone CH necessary to obtain the ratio b/a referred to was added to these two parts. This crosslinking system was employed as such, freshly prepared (Δt=O) or after having been subjected to aging at 70° C. for a period Δt of 72, 168 and 336 hours.

The spreading time (st) of the catalyzed composition was then determined by noting the time for which this composition remained in a sufficiently fluid state to spread under its own weight and thus to adopt the configuration of the internal volume of the receptacles into which it was poured.

The test employed for assessing the spreadability was as follows:

The freshly catalyzed composition (15 grams) was poured into an aluminum capsule of cylindrical shape with a diameter of 4 cm; after a time not exceeding 5 minutes its surface must be perfectly horizontal.

The catalyzed composition was converted into a silicone elastomer after several hours at ambient temperature; 24 hours (1 day) and 96 hours (4 days) after the preparation of this catalyzed composition the Shore A hardness of the elastomer formed, called SAH1 and SAH4, is measured. The results relating to the spreading times (st) in minutes and to the Shore A hardness values (SAH1 and SAH4) are reported in Table 2 below. The catalyst in the comparative example was di-n-octyltin di-2-ethylhexanoate.

In Table 2 below, C ex n shows that the catalyst employed was that obtained in Example n.

It was found that the catalysts according to the invention, in contrast to the control catalyst, endow the silicone elastomer with satisfactory hardness and spreading time values even after prolonged aging of the crosslinking system.

TABLE 2

| | | EXAMPLE | | | | | | | | | | |
|---|---|---|---|---|---|---|---|---|---|---|---|---|
| | | 5 CONTROL | | | 6 C ex 1 | | | 7 C ex 2 | | | 8 C ex 3 | | |
| | CATALYST | st | SAH1 | SAH4 | st | SAH1 | SAH4 | st | SAH1 | SAH4 | st | SAH1 | SAH4 |
| Δt | 0 | 170 | 16 | 26 | 115 | 17 | 26 | 115 | 16 | 28 | 85 | 15 | 17 |
| | 72 | 210 | 12 | 24 | 155 | 15 | 27 | 140 | 15 | 26 | 120 | 13 | 26 |
| | 168 | 290 | 6 | 23 | 210 | 12 | 27 | 190 | 13 | 26 | 150 | 10 | 26 |
| | 336 | 310 | 5 | 23 | 300 | 11 | 23 | 230 | 13 | 23 | 180 | 10 | 22 |

COMPARATIVE EXAMPLE 9 AND EXAMPLES 10 TO 12

The purpose of these Examples is to demonstrate the better natural aging behavior of the elastomers obtained from composition P$_1$ of Examples 5 to 8, catalyzed with a crosslinking system containing the catalysts (C) forming the subject of Examples 1 to 3 and partially hydrolyzed ethyl silicate, the concentration of tin catalyst (calculated as weight of metallic tin) being maintained constant.

5 parts of a crosslinking system containing 82.5 parts of partially hydrolyzed ethyl silicate and 17.5 parts of catalyst (C) were mixed with 100 parts of composition P$_1$. The amount of β-diketone CH needed to obtain the intended b/a ratio was added to these 5 parts.

The catalyzed composition was deposited on a polyethylene plaque, in the form of a layer having a thickness of 2 mm. After a period of 24 hours at rest in ambient air, the resulting elastomer film was demolded and was permitted to age at a temperature of 20° C. for various times (in months).

The Shore A hardness and the tear resistance TR (expressed in kN/m) of the above-mentioned film which had been subjected to the aging times were measured.

The results are reported in Table 3 below, where C ex n shows that the tin catalyst employed was that obtained in Example n. The control catalyst in Comparative Example 9 was di-n-octyltin di-2-ethylhexanoate.

TABLE 3

| | | AGING PERIOD (IN MONTHS) | | | | | | | | | | |
|---|---|---|---|---|---|---|---|---|---|---|---|---|
| | CATALYST | 0 MONTHS | | 1 MONTH | | 3 MONTHS | | 5 MONTHS | | 9 MONTHS | | 12 MONTHS | |
| EXAMPLE | c in n | SAH | TR | SAH | TR | SAH | TR | SAH | TR | SAH | TR | SAH | TR |
| 9 | CONTROL | 38 | 25 | 41 | 25 | 42 | 24 | 40 | 21 | 44 | 10 | 45 | 6 |
| 10 | c ex 1 | 40 | 26 | 42 | 28 | 44 | 25 | 42 | 24 | 43 | 23 | 44 | 19 |
| 11 | c ex 2 | 41 | 25 | 42 | 26 | 44 | 23 | 44 | 25 | 43 | 25 | 45 | 25 |

TABLE 3-continued

| EXAMPLE | CATALYST c in n | AGING PERIOD (IN MONTHS) | | | | | | | | | | |
|---|---|---|---|---|---|---|---|---|---|---|---|---|
| | | 0 MONTHS | | 1 MONTH | | 3 MONTHS | | 5 MONTHS | | 9 MONTHS | | 12 MONTHS | |
| | | SAH | TR | SAH | TR | SAH | TR | SAH | TR | SAH | TR | SAH | TR |
| 12 | c ex 3 | 42 | 26 | 47 | 21 | 47 | 21 | 47 | 21 | 48 | 20 | 47 | 20 |

From Table 3 it will be seen that better stability of the elastomer was realized using a catalyst in accordance with the invention.

COMPARATIVE EXAMPLE 13 AND EXAMPLE 14

The following constituents were triturated in a kneader:

(i) 100 parts of an α,ω-dihydroxydimethylpolysiloxane oil having a viscosity of 70,000 mPa.s at 25° C.;

(ii) 20 parts of a bis(trimethylsiloxy)dimethylpolysiloxane oil having a viscosity of 100 mPa.s at 25° C.;

(iii) 130 parts of calcium carbonate having a mean particle diameter of 5 micrometers; and (iv) 9 parts of a pyrogenic silica having a specific surface area of 150 m²/g.

When the mass was homogeneous, all the solution produced by mixing the following ingredients was added to it: 5.5 parts of silane of formula $Si(OCH_2CH_2OC_2H_5)_4$, 2.5 parts of silane of formula $(CH_3O)_3Si(CH_2)_3NH-CH_2CH_2NH_2$, and 0.040 part of the organic tin derivative which was prepared according to the procedure of Example 4 above.

The single-component composition thus obtained was stored in the absence of moisture in sealed aluminum tubes (Example 14); another composition, identical with the preceding, was prepared, except that the organic tin derivative employed was only dibutyltin dilaurate, and the amount employed was identical, namely, 0.040 part (comparative Example 13).

This composition was also packaged in sealed aluminum tubes. The storage stability of both compositions was monitored; for this purposes, the tubes containing them were left for 72 hours in an oven heated to 100° C..

The tubes were permitted to cool and their contents (and the contents of tubes which had not been subjected to a period of heating and had been stirred for a period of 1 month at ambient temperature) were spread in the form of a layer with a thickness of 2 mm, in the open air, on a polytetrafluoroethylene plate. The deposited layer changed into a rubbery film; 24 hours after the deposition of the layer the elastomer film was removed and the tensile properties of the elastomers were measured after aging for 7 days at ambient temperature.

The results are reported in Table 4 below:

TABLE 4

| | EXAMPLE 14 | | EXAMPLE 13 | |
|---|---|---|---|---|
| Tensile properties | Contents of the tubes stored at ambient temperature | Contents of the tubes aged 72 hrs at 100° C. | Contents of the tubes stored at ambient temperature | Contents of the tubes aged 72 hrs at 100° C. |
| Shore A hardness | 30 | 10 | 26 | — |
| Tensile strength in MPa | 1.1 | 1.0 | 1.0 | — |
| Elongation at break in % | 514 | 410 | 348 | — |

—: not measurable.

Examination of the values of the tensile properties demonstrated clearly that, in order to retain these properties with time, it was advantageous to employ the catalyst mixture according to the invention rather than di-n-butyltin dilaurate alone.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An organopolysiloxane composition of matter curable into elastomer state, comprising (1) a curable organopolysiloxane base which is an organopolysiloxane polymer and a crosslinking agent therefor, and (2) a catalytically effective amount of the product of reaction between (a) a tin salt of the formula:

$$(X)_2 SnR_1 R_2 \qquad (1)$$

in which the symbols $R_1$ and $R_2$, which may be identical or different, are each an optionally substituted, monovalent $C_1-C_{18}$ hydrocarbon radical and X is a halogen atom or a monocarboxylate radical of the formula $R_6COO$ in which the symbol $R_6$ is the same $R_1$, with (b) a β-dicarbonyl compound of the formula:

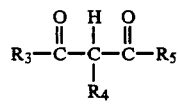

in which:

the symbols $R_3$ and $R_5$, which may be identical or different, are each a radical $R_1$ or $R_2$, a hydrogen atom, a $C_1-C_5$ alkoxy radical or an $Si(R_1)_3$ silyl radical; and the symbol $R_4$ is a hydrogen atom, or an optionally halogenated $C_1-C_{18}$ hydrocarbon radical, with the proviso that $R_4$ and $R_5$ may together form, with the carbon atoms from which they depend, a divalent $C_5-C_{12}$ cyclic hydrocarbon radical, or an optionally substituted such hydrocarbon radical bearing at least one chloro, nitro and/or cyano substituent, in a molar ratio (2)/(1) ranging from 0.01 to 100, said product of reaction being a monochelate of pentacoordinated tin of valency IV.

2. The organopolysiloxane composition as defined by claim 1, said molar ratio ranging from 1 to 3.

3. The organopolysiloxane composition as defined by claim 1 wherein said curable organopolysiloxane base comprises:
  (A) 100 parts by weight of an α, ω-dihydroxypolydiorganosiloxane polymer having a viscosity of 500 to 1,000,000 mPa.s at 25° C. and which comprises recurring units of the formula $(R_2)SiO$ where the symbols R, which may be identical or different, are hydrocarbon radicals containing from 1 to 10 carbon atoms, optionally substituted by at least one halogen atom or cyano radical;
  (B) 0.5 to 20 parts by weight of an organosilicon compound crosslinking agent containing more than two hydrolyzable groups bonded to silicon atoms, per molecule;
  (C) 0 to 250 parts by weight of inorganic filler material; and
  (D) 0 to 20 parts by weight of an adhesion promoter.

4. The organopolysiloxane composition as defined by claim 3, comprising a silane crosslinking agent B of the formula:

$$R_aSi(Z)_{4-a} \qquad (6)$$

in which R is a hydrocarbon radical containing from 1 to 10 carbon atoms and Z is N-substituted amino, N-substituted amido, N,N-disubstituted aminoxy, ketiminoxy, alkoxy, alkoxyalkylenoxy, enoxy or acyloxy, and a is 0 or 1.

5. The organopolysiloxane composition as defined by claim 1, formulated in single-component form.

6. The organopolysiloxane composition as defined by claim 1, formulated in two-component form.

* * * * *